United States Patent [19]

Bajusz et al.

[11] Patent Number: 4,478,745

[45] Date of Patent: Oct. 23, 1984

[54] T-BUTYLOXY-CARBONYL-D-PHENYLALA-NYL-L-PROLYL-L-ARGININE ALDEHYDE HEMISULFATE, D-PHENYLALANYL-L-PROLYL-L-ARGININE ALDEHYDE SULFATE AND PROCESS FOR THE PREPARATION THEREOF

[75] Inventors: Sándor Bajusz, Budapest; Erzsébet Szell née Hasenohrl, Hudapest; Éva Barabás; Dániel Bagdy, both of Budapest, all of Hungary

[73] Assignee: Richter Gedeon Vegyeszeti Gyar R.T., Budapest, Hungary

[21] Appl. No.: 484,888

[22] Filed: Apr. 14, 1983

Related U.S. Application Data

[63] Continuation-in-part of Ser. No. 337,288, Jan. 5, 1982, Pat. No. 4,399,065.

[30] Foreign Application Priority Data

Jan. 13, 1981 [HU] Hungary .................................. 70/81

[51] Int. Cl.$^3$ ........................................... C07C 103/52
[52] U.S. Cl. ............................................. 260/112.5 R
[58] Field of Search .................. 260/112.5 R; 424/177

[56] References Cited

U.S. PATENT DOCUMENTS 3,826,793  7/1981  Blomback et al. ........... 260/112.5 R
4,316,889  2/1982  Bajusz et al. ................. 260/112.5 R
4,399,065  8/1983  Basjusz et al. ............... 260/112.5 R

FOREIGN PATENT DOCUMENTS 0880844  1/1979  Belgium .

Primary Examiner—Delbert R. Phillips
Assistant Examiner—F. T. Moezie
Attorney, Agent, or Firm—Keil & Weinkauf

[57] ABSTRACT

The invention relates to t-butyloxy-carbonyl-D-phenylalanyl-L-prolyl-L-arginine aldehyde hemisulfate and D-phenylalanyl-L-prolyl-L-arginine aldehyde sulfate, which is highly stable in aqueous solution, and to a process for preparing D-phenylalanyl-L-prolyl-L-arginine aldehyde sulfate from D-phenylalanyl-L-prolyl-L-arginine aldehyde hemisulfate or $N^G$-carboxy derivative containing an acid-sensitive protecting group at its amino terminal, wherein the acid sensitive amino terminal protecting group or optionally the $N^G$-carboxy group is removed with 1 to 12 N sulfuric acid, applied in 1 to 12 equivalent amounts and the resulting free tripeptide aldehyde sulfate isolated. The D-phenylalanyl-L-prolyl-L-arginine aldehyde sulfate of the invention possesses valuable anti-coagulant activity.

1 Claim, No Drawings

T-BUTYLOXY-CARBONYL-D-PHENYLALANYL-L-PROLYL-L-ARGININE ALDEHYDE HEMISULFATE, D-PHENYLALANYL-L-PROLYL-L-ARGININE ALDEHYDE SULFATE AND PROCESS FOR THE PREPARATION THEREOF

This application is a continuation-in-part of application Ser. No. 337,288, filed Jan. 5, 1982, now U.S. Pat. No. 4,399,065.

The invention relates to t-butyloxy-carbonyl-D-phenylalanyl-L-prolyl-L-arginine aldehyde hemisulfate, D-phenylalanyl-L-prolyl-L-arginine aldehyde sulfate, highly stable in aqueous solution, and to a process for the preparation thereof.

It is known that heparin, polyanions of related structure/heparinoids/, and coumarin derivatives are being mostly applied in anticoagulant therapy at present. It is a common feature of these agents that they fail to induce direct inhibition of the proteolytic reaction, triggering blood clotting. Heparin as a catalyst accelerates the inhibitory action of one of the plasma inhibitors, antithrombin III, on the enzymes of the coagulation process, primarily that of thrombin, while coumarin derivatives are inhibiting the biosynthesis of proteins containing gamma-carboxy-glutamic acid/Gla/moieties. There are four proteins of this type which are involved in the blood coagulation process, one of them being prothrombin. Blood coagulation factors having more or less than the formal number of Gla residues, are inactive, and are not participating in the coagulation process. It should be noted, however, that this inhibition covers the synthesis of the entire range of Gla containing proteins, i.e., one of the natural inhibitors of the coagulation process, protein C (or factor XIV), is also synthesized in inactive form in the presence of courmarin derivatives, which is rather disadvantageous. It is also a characteristic feature that heparin is administered primarily in i. v. infusion, as it is practically inactive at oral application, while coumarin derivatives can only be given orally. Consequently, the effect of heparin may be registered rapidly, within a short period of time, while that of coumarin derivatives—being synthesis inhibitors—only after 24 to 36 hours.

Furthermore it is known that there are tripeptide aldehydes which also exhibit anticoagulant activity; however, contrary to the above agents they enter into direct reaction with thrombin, inhibiting its proteolytic reactions even in the absence of antithrombin III. D-phenylalanyl-L-prolyl-L-arginine aldehyde acetate, described in Hungarian Pat. No. 169,870 as well as D-phenylalanyl-L-prolyl-$N^G$-carboxy-L-arginine aldehyde, described in Belgian Pat. No. 880,844 are both potent thrombin inhibitors.

It was observed that the antithrombin potency of the above synthetic arginine-peptide aldehyde salts—especially that of compounds having a free terminal amino group—i.e. D-phenylalanyl-L-prolyl-L-arginine aldehyde acetate and hydrochloride—is varying and rapidly decreasing upon standing in aqueous solution, making therapeutical application impossible. Though the $N^G$-carboxy derivative of the free tripeptide aldehydes, i.e. D-phenylalanyl-L-prolyl-$N^G$-carboxy-L-arginine aldehyde is retaining its activity in aqueous buffer solution for 20 to 24 hours, after several days, however, there is already a significant reduction in potency and after several months there is a loss of original activity even in solid form.

The invention relates to a new salt of D-phenylalanyl-L-prolyl-L-arginine aldehyde which, contrary to hitherto known products is stable also in aqueous solution, and to a process for the preparation thereof.

It was found that the stability of diverse salts of D-phenylalanyl-L-prolyl-L-arginine aldehyde was varying in aqueous solution, i.e. isotonic salt solution, to a significant degree. In the course of our tests the peptides were dissolved in concentrations of 10 mg/ml, stored at 5° C., and the ensuing change in antithrombin activity registered for 180 days. The potency was assayed in a system containing the following components:

0.2 ml of 0.5 percent bovine fibrinogen in a 0.9 percent solution of sodium chloride, 0.1 ml of tris(hydroxymethyl)-amino-methane hydrochloride - hydrochloric acid buffer (pH 7.2) containing the peptide solution 0.1 ml of US Standard Human Thrombin (NIH, Bethesda, Md., USA), 10 Unit/ml solution.

The thrombin time of the peptide-free system is 15 s, measured in the "Schnither-Gross Coagulometer".

The activity of the tripeptide aldehyde solution was arbitrarily set up as 100, if the reaction mixture induced a fivefold relative thrombin time at a final concentration of $3.5 \times 10^{-7}$ M (in the case of the tripeptide aldehyde sulfate at 0.175 µg/ml).

The test data are summarized in Table I. It is apparent that while the activity of the corresponding hydrochloride in isotonic salt solution is starting to decrease after 5 days, and that of the acetate, citrate, tartrate and tosylate already after several days (similarly to the $N^G$-carboxy derivative of the free tripeptide aldehyde having related properties), the D-phenylalanyl-L-prolyl-L-arginine aldehyde sulfate is retaining its antithrombin activity for 90 days. In prolonged stability trials D-phenylalanyl-L-prolyl-L-arginine aldehyde sulfate proved to be stable even for 180 days in aqueous medium, and in solid form it similarly failed to lose activity for 6 months.

TABLE 1

Antithrombin activity of tripeptide aldehyde salts in isotonic salt solution

| Peptide aldehyde[a] | Relative activity[b] after | | | | | | |
|---|---|---|---|---|---|---|---|
| | 0 | 5 | 10 | 15 | 20 | 40 | 90 |
| | days | | | | | | |
| D-Phe—Pro—Arg—H.2 CH$_3$COOH[cd] | 70-50 | 60-40 | 40-30 | 40-30 | 40-30 | 35-25 | 30-20 |
| D-Phe—Pro—Arg—H.2HCl[e] | 90-60 | 90-60 | 80-50 | 70-40 | 60-40 | 50-30 | 40-30 |
| D-Phe—Pro—Arg(COOH)—H[e] | 100 | 80 | 60 | 50 | 30 | 25 | 20 |

TABLE 1-continued

| Antithrombin activity of tripeptide aldehyde salts in isotonic salt solution | | | | | | | |
|---|---|---|---|---|---|---|---|
| | Relative activity[b] after | | | | | | |
| | 0 | 5 | 10 | 15 | 20 | 40 | 90 |
| Peptide aldehyde[a] | days | | | | | | |
| D-Phe—Pro—Arg—H.H$_2$SO$_4$[f] | 100 | 100 | 100 | 100 | 100 | 100 | 100 |

[a]The abbreviations used conform to those established in the literature [i.e. J. Biol. Chem. 247, 977 (1972)], Z representing benzyloxycarbonyl, Arg(COOH) and, resp., Arg(Z) representing N$^G$—carboxy and N$^G$—benzyloxycarbonyl-L-arginine groups, resp.
[b]The peptide aldehyde inducing a fivefold relative thrombin time at a final concentration of $3.5 \times 10^{-7}$ M in the reaction mixture has an antithrombin activity of 100.
[c]Product obtained by the hydrogenolysis of Z—D-Phe—Pro—Arg(Z)—H in the presence of one equivalent amount of an acid.
[d]The antithrombin activity of the corresponding citrate, tartrate and tosylate is changing similarly to that of the acetate.
[e]Product synthesized according to the process described in Belgian Patent 880 844.
[f]Product prepared according to the process of the present invention.

In order to simulate physiological conditions the antithrombin activity of the tripeptide aldehyde salts as well as that of the carbamic acid derivatives was tested also on human plasma in the following system:
0.2 ml of human citrate plasma,
0.1 ml of tris(hydroxymethyl)-amino-methane hydrochloride - hydrochloric acid buffer solution (pH 7.2) containing the peptide solution, and
0.1 ml of US Standard Human Thrombin (NIH, Bethesda Md., USA), 10 Units/ml solution.
The thrombin time of the peptide-free system is 15 s, measured in the "Schnither-Gross Coagulometer".

TABLE 2

| Antithrombin activity of tripeptide aldehyde derivatives in human plasma | | |
|---|---|---|
| Peptide aldehyde | Amount of peptide ($\mu$g/ml+) required to increase thrombin time twofold immediately following dissolution of the peptide | Relative activity |
| D-Phe—Pro—Arg—H.H$_2$SO$_4$ | 0.020 | 100 |
| D-Phe—Pro—Arg(COOH)—H | 0.042 | 45 |
| D-Phe—Pro—Arg—H.2 CH$_3$COOH | 0.065–0.140 | 35–14 |
| D-Phe—Pro—Arg—H.2 HCl | 0.060–0.130 | 33–15 |
| Heparin[a] | 0.105 | 19 |

[a]Value measured with commercial heparin (132.2 U/mg, U.S. Ph. XVII).
+Amount of the peptide in the reaction mixture.

The data of Table 2 clearly demonstrate that the amount of peptide required to achieve a twofold thrombin time increase compared to the control varies according to the batch used in the case of the acetate and the hydrochloride salts, and is a manifold—in the case of the carbamic acid derivative twofold—of the amount required of the tripeptide aldehyde sulfate.

The in vivo trial of the tripeptide aldehyde derivatives is summarized in Table 3. D-Phenylalanyl-L-prolyl-L-arginine aldehyde sulfate has a significant antithrombin potency in vivo. At intravenous and subcutaneous application its efficacy is in the range of that of heparin, generally applied in therapy, however, it has major advantages compared to it. While heparin, given orally, is inactive, therapeutic effect may be achieved with oral doses of 25 mg/kg of the tripeptide aldehyde sulfate (but only with 50 mg/kg doses of the carbamic acid derivative).

TABLE 3

| In vivo trials Dose required for therapeutic effect[a] | | | | | | |
|---|---|---|---|---|---|---|
| | mg/kg/hour | | mg/kg | | | |
| | i.v. infusion | | s. c. | | p. o. | |
| Peptide aldehyde | rabbit | dog | rabbit | dog | rabbit | dog |
| D-Phe—Pro—Arg—H. 2 CH$_3$COOH | — | — | — | — | 100 | 100 |
| D-Phe—Pro—Arg—H. 2 HCl | — | — | — | — | — | 100 |
| D-Phe—Pro—Arg(COOH)—H | — | 3.0 | 10.0 | 6.0 | 50 | 50 |
| D-Phe—Pro—Arg—H. H$_2$SO$_4$ | 1.0 | 0.5 | 6.0 | 6.0 | 25 | 25 |
| Heparin | 0.6 | 0.5 | 5.0 | 2.0 | — | — |

[a]The therapeutic effect is characterized by the dose required to prolong thrombin time in the whole blood 1.5 to 2.5 fold [Nies, A. S. (1978) in Clinical Pharmacology (Melmon, K. L. and Morrelli, F. F. Eds.) 2nd Ed. pp. 303 to 306, Macmillan Publ. Co. Inc. New York; and Versraete, and M. Verwilghen, R. (1980) in Drug Treatment, Principles and Practice of Clinical Pharmacology and Therapeutics, 2nd Ed., Avery G. S. Ed. (1980) pp. 889 to 952, Edinburgh and London].

The toxicity data of D-phenylalanyl-L-prolyl-L-arginine aldehyde sulfate are also more favourable than those of either the acetate or the carbamic acid derivative. The acute toxicity data are summarized in Table 4; this amounted in the case of the tripeptide aldehyde sulfate at oral administration to 2 g/kg.

TABLE 4

| Acute toxicity data in mice | | | | |
|---|---|---|---|---|
| | LD$_{50}$ mg/kg | | | |
| Peptide aldehyde | i.v. bolus | i.p. | s.c. | p.o. |
| D-Phe—Pro—Arg—H.2CH$_3$COOH | 9 | 38 | — | 960 |
| D-Phe—Pro—Arg(COOH)—H[a] | — | — | — | 1200 |
| D-Phe—Pro—Arg—H.H$_2$SO$_4$ | 45[b] | 230 | 1800 | >2000 |
| Heparin | no literature data available | | | |

[a]Due to poor solubility the toxicity data obtained at applications other than p.o. are rather uncertain.
[b]At intravenous infusion the LD$_{50}$ amounted to 58 mg/kg in the rabbit.

Considering the low toxocity and high potency of D-phenylalanyl-L-prolyl-L-arginine aldehyde sulfate, the therapeutic index, including both, and being the most characteristic indicator of the therapeutical value of a drug, is more favourable than those of the other tripeptide aldehyde derivatives.

On the basis of intravenous infusion trials in dogs the dose of the human intravenous infusion was established as 1-2 mg(kg)hour.

It was found that D-phenylalanyl-L-prolyl-L-arginine aldehyde sulfate may be prepared by a method known per se, by submitting benzyloxycarbonyl-D-phenylalanyl-L-prolyl-$N^G$-benzyloxycarbonyl-L-arginine aldehyde (Z-D-Phe-Pro-Arg(Z)-H) to hydrogenolysis in the presence of equivalent amounts of sulfuric acid. Furthermore it may be simply prepared in sufficient purity from its acid sensitive derivative containing triphenylmethyl or t-alkyloxycarbonyl protective group, i.e. from t-butyloxycarbonyl-D-phenylalanyl-L-prolyl-L-arginine aldehyde hemisulfate or t-butyloxycarbonyl-D-phenylalanyl-L-prolyl-$N^G$-carboxy-L-arginine aldehyde with 1 to 12 N sulfuric acid. At the same time the following methods, known per se, failed to furnish satisfactory results:

a. Acidolysis of the t-butyloxycarbonyl group with sulfuric acid dissolved in acetic acid [Beyerman et al.: in Peptides, 1970 (Ed.: H. Nesvadba), p. 138., North Holland, Amsterdam, 1973].

b. Direct conversion of the D-Phe-Pro-Arg(COOH)-H carbamic acid derivative of Belgian Pat. No. 880,844 with sulfuric acid into the unprotected tripeptide aldehyde sulfate.

c. Transformation of diverse other unprotected tripeptide aldehyde salts, i.e. of D-phenylalanyl-L-prolyl-L-arginine aldehyde acetate of Hungarian Pat. No. 169,870 into its sulfate either with an ion-exchange resin or with sulfuric acid.

The products obtained with either of the a–c methods proved to be of poor homogeneity and/or stability in aqueous solution.

Based on the above the invention relates to D-phenylalanyl-L-prolyl-L-arginine aldehyde sulfate and to a process for preparing it from D-phenylalanyl-L-prolyl-L-arginine aldehyde hemisulfate or D-phenylalanyl-L-prolyl-$N^G$-carboxy-L-arginine aldehyde, containing an acid sensitive protecting group at its amino terminal, in which the acid sensitive amino terminal protecting group or optionally the $N^G$-carboxy group is removed with 1 to 12 N sulfuric acid, applied in 1 to 12 equivalent amounts, and the resulting free tripeptide aldehyde sulfate is isolated.

According to a preferred process of the invention the L-arginine lactam, protected at its guanidino group with a benzyloxycarbonyl group, is condensed with t-butyloxycarbonyl-D-phenylalanyl-L-proline, the resulting blocked tripeptide lactam is reduced, and the benzyloxycarbonyl group at the guanidino group of the protected tripeptide aldehyde obtained is submitted to hydrogenolysis in ethanol or tetrahydrofuran containing 30 to 40 percent of water, in the presence of an equivalent amount of sulfuric acid. The resulting tripeptide aldehyde hemisulfate, still protected at its amino terminal, is dissolved in 8 to 12 equivalents, preferably 10 equivalents of 4 to 6 N, preferably 5 N sulfuric acid, and heated for 20 to 40 minutes, preferably 30 minutes to 40° to 60° C., preferably to 50° C., the solution is subsequently neutralized with calcium carbonate, filtered, and preferably freeze-dried.

The product prepared in this way may eventually contain 4 to 6 percent of calcium sulfate, which however does not affect either its biological activity or its therapeutic application.

The invention is further illustrated by but not limited to the following Examples.

The $R_F$ values in the Examples are determined by silica gel thin-layer chromatography (Kieselgel G, Reanal, Budapest) in the following systems:
1. Ethyl acetate-pyridine-acetic acid-water - 480:20:6:11
2. Ethyl acetate-pyridine-acetic acid-water - 60:20:6:11
3. Ethyl acetate-pyridine-acetic acid-water - 30:20:6:11.

EXAMPLE 1

D-Phenylalanyl-L-prolyl-L-arginine aldehyde sulfate t-Butyloxycarbonyl-D-phenylalanyl-L-prolyl-L-arginine aldehyde hemisulfate (2.74 g, 5 mmoles) is dissolved in water (5 ml), 10 N sulfuric acid (5 ml) added at constant stirring, and the mixture heated to 50° C. The solution is stirred for 15 minutes at 50° C., then diluted with ice water (25 ml), and its pH adjusted to 6.5 with calcium carbonate (about 2.25 g) at ice cooling. The precipitated calcium sulfate is filtered, and washed twice with water (5 ml). The filtrate is extracted twice with N butanol (10 ml), concentrated to about 30 ml, filtered, if necessary, and freeze dried. Yield 2.25 g (79 percent) of the title product, containing 4.8 percent of calcium sulfate.

$R_F$=0.35 to 0.40.

$[\alpha]_D^{20}= -117\pm 1°$ (c=1, water).

Analysis calculated for $C_{20}H_{30}O_3N_6 \cdot H_2SO_4 \cdot 3 H_2O \cdot 0.2$ $CaSO_4$(565.85): Calculated: C 42.45, H 6.77, N 14.85, $SO_4$ 20.37, Ca 1.41, $H_2O$ 9.55 percent. Found: C 42.2, H 6.9, N 14.85, $SO_4$ 19.8, Ca 1.3, $H_2O$ 9.75 percent.

The starting materials are synthesized according to the following procedure:

STEP 1 t-Butyloxycarbonyl-D-phenylalanyl-L-prolyl-$N^G$-benzyloxycarbonyl-L-arginine lactam t-Butyloxycarbonyl-$N^G$-benzyloxycarbonyl-L-arginine lactam (8.6 g, 22 mmoles, Belgian Pat. No. 880,844) is suspended in ethyl acetate (20 ml), and at 5° C. and constant stirring a solution of 4M hydrochloric acid in ethyl acetate (40 ml) added to it. The reaction mixture is stirred for 30 minutes under ice cooling, diluted with cool ethyl acetate (100 ml), the precipitate formed filtered, washed with ethyl acetate, and dried at reduced pressure in an exsiccator over potassium hydroxide. The resulting $N^G$-benzyloxycarbonyl-L-arginine lactam hydrochloride is dissolved in dimethylformamide (20 ml), and at -10° C. triethylamine (6.2 ml, 44 mmoles) added to it. The suspension formed is added to the following mixed anhydride.

t-Butyloxycarbonyl-D-phenylalanyl-L-proline [U. Ludescher and R. Schwyzer: Helv Chim. Acta 55, 2052 (1972)] (7.25 g, 20 mmoles) and N-methyl-morpholine (2.22 ml, 20 mmoles) are dissolved in dimethylformamide (20 ml). The solution is cooled to -15° C., chloroformic acid isobutyl ester (2.64 ml, 20 mmoles) is added to it at stirring and then after 5 minutes the above solution in dimethylformamide is added. The stirring is continued for 1 hour at -15° C., and for 1 hour at 0° C., then the reaction mixture is diluted with benzene (30 ml), the precipitated salts are filtered and washed twice with benzene (10 ml). The solution of benzene-dimethylformamide is diluted with water (50 ml) and the phases are separated. The aqueous layer is extracted twice with benzene (10 ml), then the combined benzene extracts are washed three times with a solution of 10 percent sodium carbonate (30 ml), water (30 ml), three times with 0.5 N sulfuric acid (30 ml), twice with water (30 ml), and the solution evaporated at reduced pressure following drying over anhydrous sodium sulfate. The evaporation residue is homogenized with petroleum ether, filtered, washed with petroleum ether and air-dried. Yield: 9.65 g (76 percent) of the title product.
$R_F = 0.81$ to 0.89.

STEP 2 t-Butyloxycarbonyl-D-phenylalanyl-L-prolyl-$N^G$-benzyloxycarbonyl-L-arginine aldehyde The tripeptide lactam (9.52 g, 15 mmoles, Step 1) is dissolved in tetrahydrofuran (45 ml), and at $-20°$ C. and vigorous stirring lithium aluminium hydride (11.25 mmoles) added to it in tetrahydrofuran (about 28 ml of a 0.4 M solution). The proceeding of the reduction is controlled by thin-layer chromatography [$R_F^1 = 0.71$ to 0.77 (lactam) and $R_F^1 = 0.31$ to 0.39 (aldehyde)]. If necessary, a further portion of the hydride solution is added. When the reaction is concluded the tetrahydrofuran solution is cautiously acidified with 0.5 N sulfuric acid to pH 3, then diluted in such a way that no precipitation occurs (about 100 ml). The aqueous tetrahydrofuran solution is extracted three times with methylene chloride (75 ml), and the combined methylene chloride extracts wahsed three times with a solution of 10 percent sodium carbonate (10 ml), then twice with water (10 ml). The methylene chloride solution is subsequently dried over anhydrous sodium sulfate and evaporated at reduced pressure. The evaporation residue is dissolved in benzene (50 ml) and the solution repeatedly evaporated at reduced pressure. Then the dissolving and evaporating is repeated once more. The evaporation residue is worked up with ether, filtered, washed with diethyl ether and air-dried. Yield: 6.9 g (72 percent) of the title product.
$R_F^1 = 0.3$ to 0.4.

STEP 3 t-Butyloxycarbonyl-D-phenylalanyl-L-prolyl-L-arginine aldehyde hemisulfate

Protected tripeptide aldehyde (6.4 g, 10 mmoles, Step 2) is dissolved in a mixture of water (50 ml), tetrahydrofuran (50 ml) and 1 N sulfuric acid (10 ml) and submitted to hydrogenolysis in the presence of a 10 percent palladium charcoal catalyst (1 g). The proceeding of the reaction is controlled by thin-layer chromatography /$R_F^2 = 0.95$ to 1.0 [tripeptide aldehyde protected at its guanidino group/and $R_F^2 = 0.45$ to 0.54 (unprotected tripeptide aldehyde)]. After the reaction is concluded the catalyst is filtered, washed with a 50 percent aqueous tetrahydrofuran solution (30 ml), and the combined filtrates concentrated at reduced pressure to about 60 ml. The residue is extracted four times with n-butanol. The n-butanol layers are combined and evaporated at reduced pressure to dryness. The evaporation residue is worked up with a mixture of diethyl ether - diisopropyl ether (1:1), filtered, washed with the above mixture, then dried at reduced pressure in an exsiccator. Yield: 4.4 g (80 percent) of the title compound.
$R_F^2 = 0.45$ to 0.54.
$[\alpha]_D^{20} = -65 \pm 1°$ (c=1, water).
Analysis calculated for $C_{25}H_{38}O_5N_6 \cdot 0.5\ H_2SO_4$ (551.64): Calculated: C 54.43, H 7.13, N 15.23, $SO_4$ 8.71 percent. Found: C 54.5, H 7.3, N 15.2, $SO_4$ 8.7 percent.

EXAMPLE 2

D-Phenylalanyl-L-prolyl-L-arginine aldehyde sulfate t-Butyloxycarbonyl-D-phenylalanyl-L-prolyl-$N^G$-carboxy-L-arginine aldehyde (2.85 g, 5 mmole) is dissolved in water (5 ml), 10 N sulfuric acid (5 ml) added to it and heated to 50° C. The solution is stirred for 15 minutes at 50° C., then diluted with ice water (25 ml), and its pH adjusted to 6.5 with solid calcium hydroxide (about 1.6 grams) under ice cooling. The precipitated calcium sulfate is filtered and washed twice with water (5 ml). The filtrate is extracted twice with n-butanol (10 ml), concentrated at reduced pressure to about 30 ml, filtered, if necessary, and then freeze-dried. Yield: 2.3 g (81 percent) of the title compound, containing 4.9 percent of calcium sulfate.
$R_F^3 = 0.35$ to 0.40.
$[\alpha]_D^{20} = -117 \pm 1°$ (c=1, water).
The starting material is prepared according to the following procedure:

t-Butyloxycarbonyl-D-phenylalanyl-L-prolyl-$N^G$-benzyloxycarbonyl-L-arginine aldehyde (6.4 g, 10 mmoles, Example 1, Step 2) is dissolved in 75 percent aqueous ethanol (100 ml), and submitted to hydrogenolysis in the presence of a 10 percent palladium charcoal catalyst (1 g). The progress of the reaction is controlled by thin-layer chromatography [$R_F^2 = 0.90$ to 0.95 (protected tripeptide aldehyde)and 0.45 to 0.55 ($N^G$-carboxy derivative)]. At the end of the reaction the catalyst is filtered, washed with water (30 ml), and the filtrate concentrated to 30-40 ml at reduced pressure. The residue is diluted with water (100 ml), extracted twice with methylene chloride (20 ml), and freeze dried. Yield: 5.1 g (85 percent) of the title product.
$R_F^2 = 0.45$ to 0.55.
Amino acid analysis: Phe=0.96; Pro=1 (reference amino acid). M. w. according to the amino acid analysis: 570.

EXAMPLE 3

Preparation of a pharmaceutical composition

The 2-ampoule preparation suitable for 6 or 12 hour intravenous infusion is prepared according to the following:

D-Phenylalanyl-L-prolyl-L-arginine aldehyde sulfate (420–840 mg) and human albumin (40–80 mg) are submitted to joint freeze-drying. The contents of the freeze dried ampoule are dissolved prior to use in sterile, germ-free isotonic salt solution (100–200 ml).

What we claim is:

1. tert.-butyloxy-carbonyl-D-phenylalanyl-L-prolyl-L-arginine aldehyde hemisulfate.

* * * * *